(12) United States Patent
Ferrante et al.

(10) Patent No.: US 11,860,151 B2
(45) Date of Patent: Jan. 2, 2024

(54) METHOD FOR THE EXTRACTION AND THE DETERMINATION OF MICROPLASTICS IN SAMPLES WITH ORGANIC AND INORGANIC MATRICES

(71) Applicants: Margherita Anna Letizia Ferrante, Acireale (IT); Gea Marzia Stefania Oliveri Conti, Catania (IT); Pietro Zuccarello, Mascalucia (IT)

(72) Inventors: Margherita Anna Letizia Ferrante, Acireale (IT); Gea Marzia Stefania Oliveri Conti, Catania (IT); Pietro Zuccarello, Mascalucia (IT)

( * ) Notice: Subject to any disclaimer, the term of this patent is extended or adjusted under 35 U.S.C. 154(b) by 486 days.

(21) Appl. No.: 16/978,972

(22) PCT Filed: Mar. 7, 2019

(86) PCT No.: PCT/IB2019/051838
§ 371 (c)(1),
(2) Date: Sep. 8, 2020

(87) PCT Pub. No.: WO2019/171312
PCT Pub. Date: Sep. 12, 2019

(65) Prior Publication Data
US 2020/0408734 A1    Dec. 31, 2020

(30) Foreign Application Priority Data
Mar. 7, 2018   (IT) ..................... 102018000003337

(51) Int. Cl.
*G01N 33/44* (2006.01)
*G01N 1/40* (2006.01)

(52) U.S. Cl.
CPC ......... *G01N 33/442* (2013.01); *G01N 1/4044* (2013.01); *G01N 1/4055* (2013.01); *G01N 1/4077* (2013.01); *G01N 2001/4061* (2013.01); *G01N 2001/4088* (2013.01)

(58) Field of Classification Search
CPC ...... G01N 1/34; G01N 1/4044; G01N 1/4055; G01N 1/4077; G01N 2001/4061; G01N 2001/4088; G01N 33/442
See application file for complete search history.

(56) References Cited

PUBLICATIONS

Ashton et al, "Association of metals with plastic production pellets in the marine environment", Marine Pollution Bulletin 60 (2010) 2050-2055. (Year: 2010).*
Miller et al, "Recovering microplastics from marine samples: A review of current practices", Marine Pollution Bulletin vol. 123, Issues 1-2, Oct. 15, 2017, pp. 6-18 (Year: 2017).*

(Continued)

*Primary Examiner* — Jennifer Wecker
(74) *Attorney, Agent, or Firm* — HOLLAND & HART LLP

(57) ABSTRACT

Method for the extraction and the determination of microplastics in samples with organic and inorganic matrices, including the fundamental stages of: sampling and pre-treatment, acid digestion of the sample, extraction of microplastics in liquid phase, identification and quantification of the microplastics; and characterized by the fact of measuring the dimension and counting a plurality of microplastics, as the reading area measures 1 mm², by means of electronic microscope coupled with energy dispersive X-ray analysis.

10 Claims, 8 Drawing Sheets

600 micrometer    Electron Image 1

(56) References Cited

PUBLICATIONS

Silva et al, "Microplastics in the environment: Challenges in analytical chemistry—A review", Analytica Chimica Acta 1017 (2018) 1-19. (Year: 2018).*

Narayan: Spectroscopic and chromatographic quantification of an antioxidant-stabilized ultrahigh-molecular-weight polyethylene, Clin Orthop Relat Res. Mar. 2015, 8 pgs.

Vesely: Simple colorimetric methods for determination of submilligram amounts of ultra-high molecular weight polyethylene wear particles, Acta Biomater. May 2012, 4 pgs.

Armstrong: Stir bar sorptive extraction combined with GC-MS/MS for determination of low level leachable components from implantable medical devices, J Pharm Biomed Anal. Feb. 23, 2013, 9 pgs.

Choudhury: Mechanical wear and oxidative degradation analysis of retrieved ultra-high molecular weight polyethylene acetabular cups. J Mech Behav Biomed Mater. Mar. 2018, 28 pgs.

Sosna: Polyethylene disease Acta Chir Orthop Traumatol Cech. 2003, 2 pgs.

Kandahari: A review of UHMWPE wear-induced osteolysis: the role for early detection of the immune response; Bone Res. Jul. 12, 2016, 13 pgs.

Wright: Plastic and Human Health: A Micro Issue? Environ SciTechnol. Jun. 20, 2017, 15 pgs.

Pokorny: Method for assessment of distribution of UHMWPE wear particles in periprosthetic tissues in total hip arthroplasty, Acta Chir Orthop Traumatol Cech. Aug. 2006, 8 pgs.

Fuller: A Procedure for Measuring Microplastics using Pressurized Fluid Extraction, Environmental Science & Technology, vol. 50, No. 11, May 24, 2016 (May 24, 2016), 7 pgs.

* cited by examiner

600 micrometer    Electron Image 1

10 micrometer    Electron Image 1

10 micrometer    Electron Image 1

20 micrometer    Electron Image 1

METHOD FOR THE EXTRACTION AND THE DETERMINATION OF MICROPLASTICS IN SAMPLES WITH ORGANIC AND INORGANIC MATRICES

This invention refers to a method for extracting microplastics from organic and inorganic matrices and the determination of their quantities and qualities. More specifically it provides a method for the extraction, identification, and quantification of microplastics in polyethylene, ultra high molecular weight polyethylene (UHMWPE), polycarbonate, polyethylene terephthalate (PET) and polyvinyl chloride (PVC) in samples of organic and inorganic matrices.

The study and analysis of microplastics has gained significant importance in both medical settings and in relation to environmental issues. As of today, the effects of microplastics on a systemic level are totally unknown, for example on the cardio-circulatory system, as well as their contribution in the onset of neuro-degenerative and neoplastic diseases.

Instead, from a clinical viewpoint, the issues connected to the wear of medical devices are known. For example, metal-polyethylene and ceramic-polyethylene arthroplasty are widely used in prosthetic replacement with excellent results from a biomechanical point of view. The debris resulting from the wear of polyethylene were studied for their effects on an articular level and there seems to be a correlation between the state of wear of the prosthetic component and the osteolysis of the periprosthetic bone, triggered by a chronic inflammatory reaction to the foreign body (Choudhury et al, 2018).

It is known that the osteolysis induced by wear in ultra high molecular weight polyethylene is the process by which the prosthetic debris released mechanically by the surface of the prosthetic articulation induce an immune response that promotes the catabolism of the bone with the consequential loosening of the prosthetic with potential breakage or fractures. Kandahari A M et al (2016) describe an imaging module for positron emission tomography, specific for macrophages, which is promising in early diagnosis of the disease and in the localization of the treatment. However, the system is complex and costly, as well as applicable only in the field of medicine.

A Stir Bar Sorptive Extraction (SBSE) combined with GC-MS/MS for determining low levels of components that detach from implantable medical devices is described by Armstrong B L et al (2012); the method describes multiple detection confirmed by the determination of degradation products deriving from orthopedic knee inserts in ultra high molecular weight polyethylene. However, the chromatographic method used is different than described in the present invention and the application is more complex.

Other methods of determining polyethylene particles are described in the literature, like a method for counting the particles based on the "light scattering" principle described by Pokorný et al (2006) to the specific application to periprosthetic tissues in total arthroplasty of the hip. The method is very costly and the preparation of the sample is not very reproducible.

Sosna et al. (2003) describe a method for identifying polyethylene particles in tissues and visualizing them following total dissolution of the organic structures in nitric acid. The method uses specific filters, is very costly and not very reproducible.

A spectroscopic and chromatographic method for quantifying ultra high molecular weight polyethylene stabilized with anti-oxidant is described by Narayan (2015). More specifically, the UHMWPE (ultra high molecular weight polyethylene) particles are quantified with the application of the FTIR (Fourier Transform Infrared) spectroscopy and UV-Vis. The chemical by-products generated by the gamma irradiation of PBHP are identified by using gas chromatography combined with mass spectrometry followed by a second stage mass spectrometry (GC-MS/MS). The method proposed by Narayan (2015) is different from the one described in the invention herein, as it entails the use of polyethylene with added alpha-tocopherol and, furthermore, is based on the use of other detection techniques.

Finally, Vesely et al. (2012) describe colorimetric methods for determining quantities less than a milligram of particles deriving from wear of ultra high molecular weight polyethylene. These methods are based on irreversible links of the bovine serum albumin combined with fluorescein or Oil Red O hydrophobic colorant for the wear of particles.

Of great scientific interest is the current problem of microplastic contamination, including the UHMWPE particles, of all the environmental and food matrices, that are irremediably altering the biotic system and the food chains, from the simplest to the most complex, with a lack of scientific information about the effects of chronic exposure in both animal species and on humans (Wright et al, 2017).

Moreover, the patent document CN102353618A describes a method for determining the quality of the distribution of the weight of the ultra high molecular weight polyethylene (UHMWPE); the patent makes reference to a set of methods for the comparison and the evaluation of the molecular distribution of UHMWPE, taking into account dependence on the viscosity and solubility.

In the light of what has been considered here thus far, it therefore constitutes the scope of this invention to provide a method for the extraction, the identification and the quantification of the microplastics belonging to the group comprising polyethylene, ultra high molecular weight polyethylene (UHMWPE), polycarbonate, polyethylene terephthalate (PET), polyvinyl chloride (PVC), their mixtures and by-products, in samples of organic and inorganic matrices. The present invention provides a method based on the acid digestion of the sample, extraction of the microplastics with a conventional method defined as liquid-liquid and the subsequent identification and quantification by means of a scanning electronic microscope (SEM) coupled with an X-ray microanalysis. The present invention provides a method for the quantification of microplastic particles with a diameter less than 500 micron, preferably less than 100 microns, and even more preferably with a diameter between 1 and 5 microns, so under the limit of 10 microns generally reported in the literature.

A further scope of the present invention is to provide a method that does not use particular filtration methods and/or very costly polyethylene filters, which is applicable to a wide range of matrices, both organic and inorganic, and in which the preparation of the sample is much less costly compared to other known state-of-the-art methodologies.

Indeed, the present method provides the use of inexpensive glassware and solvents that are easily found on the market. Moreover, the method minimizes both the contamination of the samples during the preparatory phase as well as interference in the instrumental response during the analytical phase, in that filters in polycarbonate or substances the chemical composition of which are similar or equal to that of the microplastic particles in question are never used.

Other aspects of this invention, including the embodiments and the applications of use on organic and inorganic matrices are described in the successive claims attached.

The aforementioned claims are understood to have been included herein.

The present invention is more evident in the detailed description that follows, with reference to the table attached, which illustrate an embodiment of the method for the extraction and the determination of microplastics in samples with organic and inorganic matrices, in which:

FIG. 3 is the screen of the results of the quantitative analyses on the polyethylene particles conducted by means of dedicated Microplast software;

FIG. 4 is another screen of the results of the quantitative analyses on the polyethylene particles conducted by means of dedicated Microplast software;

FIG. 5 is an additional screen of the results of the quantitative analyses on the polyethylene particles conducted by means of dedicated Microplast software;

Below is the description of a form of exemplary actuation, and as such not limiting, of the method for the extraction and the determination of microplastics in samples with organic and inorganic matrices.

DESCRIPTION OF THE INVENTION

Figure 1:
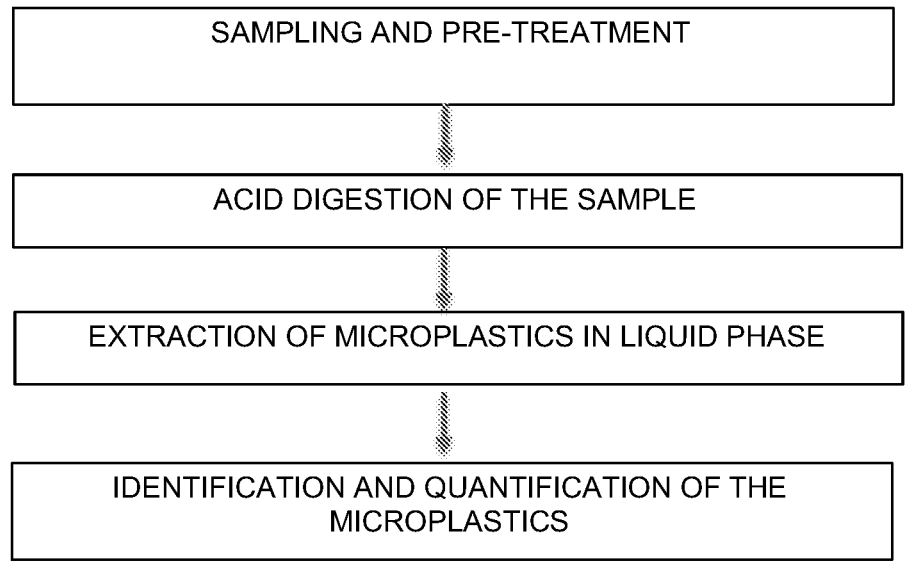
FIG. 1 is the block diagram of the fundamental stages of the method of the invention.

In reference to FIG. 1, the method for the extraction and determination of microplastics in samples with organic and inorganic matrices comprises the following fundamental stages:
a) sampling and pre-treatment,
b) acid digestion of the sample,
c) extraction of microplastics during the liquid phase,
d) identification and quantification of the microplastics.

The method inherent to this invention is applied to the extraction and determination of microplastics belonging to the group comprising: polyethylene, ultra high molecular weight polyethylene (UHMWPE), polycarbonate, polyethylene terephthalate (PET) and polyvinyl chloride (PVC) in samples of organic and inorganic matrices. Said microplastics have dimensions less than 500 μm, more specifically with dimension less than 100 μm, and even more specifically with dimensions between 1 and 5 μm.

In the processing of the method inherent to this invention, any sample will be implicitly considered a gram or a milliliter if not otherwise specified.

Said sampling stage provides the selection of samples with a watery base or of an organic matrix comprised in the group consisting of human, plant, and animal biological tissues and liquids, pharmaceuticals, cosmetics, foods, mineral waters, waters destined for human consumption, ground waters, surface waters, sea waters, waters from pools and aquaculture installations, urban and industrial, and sewage, liquid wastes.

Alternatively, said sampling stage provides the selection of airborne samples or soil samples.

Conveniently, said acid digestion state or mineralization of the sample with organic or inorganic matrices provides the treatment with strong acid, in a 1:1 m/v or v/v ratio with the abovementioned sample, for a duration of at least 24 hours at a temperature of 60° C. Said strong acid is selected from the group comprising hydrochloric acid, nitric acid, and sulphuric acid.

Said extraction stage of the microplastics includes the following phases:
1. mix an aliquot of ultra-pure water with said sample treated with strong acid in a ratio of 1:3 m/v or v/v, to obtain a liquid mixture;
2. mix a first aliquot of non-polar halogenated solvent with said liquid mixture in a ratio of 1:3 m/v or v/v, to obtain a heterogeneous liquid mixture;
3. agitate said heterogeneous liquid mixture for 30 s and centrifuge it at 4000 rpm for 15 minutes to obtain two fractions: A and B, in which fraction A is watery and fraction B is organic;
4. separate the watery fraction A from the organic fraction B;
5. add a second aliquot of non-polar halogenated solvent to the watery fraction A to obtain a second heterogeneous mixture;
6. agitate said second heterogeneous liquid mixture for 30 s and centrifuge it at 4000 rpm for 15 minutes to obtain two liquid phases: C and D, in which fraction C is watery and fraction D is organic;
7. recombine the organic fractions B and D and then evaporate to dryness at a temperature of 70° C., to obtain an extract of microplastics;
8. Suspend said extract of microplastics in acetonitrile with a volume between 100 and 500 microliters.

Said non-polar halogenated solvent is selected from the group that includes dichloromethane (DCM) and chloroform. The agitation carried out in phases 3 and 6 of the extraction stage is conveniently done with a vortex for the duration of 30 s.

Said stage of identification and quantification of the microplastics provides the transfer of said extract of the microplastics suspended in acetonitrile onto a metallic support, preferably a stub of aluminum for scanning electronic microscope (SEM Specimen Stub) with a diameter of 25 mm, taking care to distribute the extract onto the entire surface of the stub. Where the saturation of the stub surface is evident, the volume of acetonitrile is increased and more stubs are used. Then it is necessary to wait for the evaporation of the acetonitrile, taking care not to overturn the stub, preventing the particles from slipping off or modifying their dispersion. Finally, the stub is subjected to metallization with gold and inserted into the positioning chamber of the SEM samples for successive identification and quantification of the microplastics by means of electronic microscopy combined with energy dispersive X-ray, more specifically through scanning electronic microscope (SEM) combined with an Energy Dispersive X-ray Analysis (EDX).

The identification and quantification of microplastics is conducted in a total reading area within the stub of 1 mm$^2$, corresponding to a total of 228 fields at 1500 enlargement. Conveniently, the number of fields is reduced in case of an abundance of particles. The stage of identification and quantification of the microplastics calls for microanalytic acquisition phase (or the reading and recognition of the particle) and the phase of measurement and counting (or determination of the dimensions of the particle and the count). The microanalytical acquisition phase provides the verification of the chemical structure of the microplastics constituted exclusively by carbon. More specifically, it provides the determination and count of the microplastic of any dimension and form within the field of observation without discriminating position, measuring the length and width of each microplastic particle (FIG. 6-10).

Figure 3:
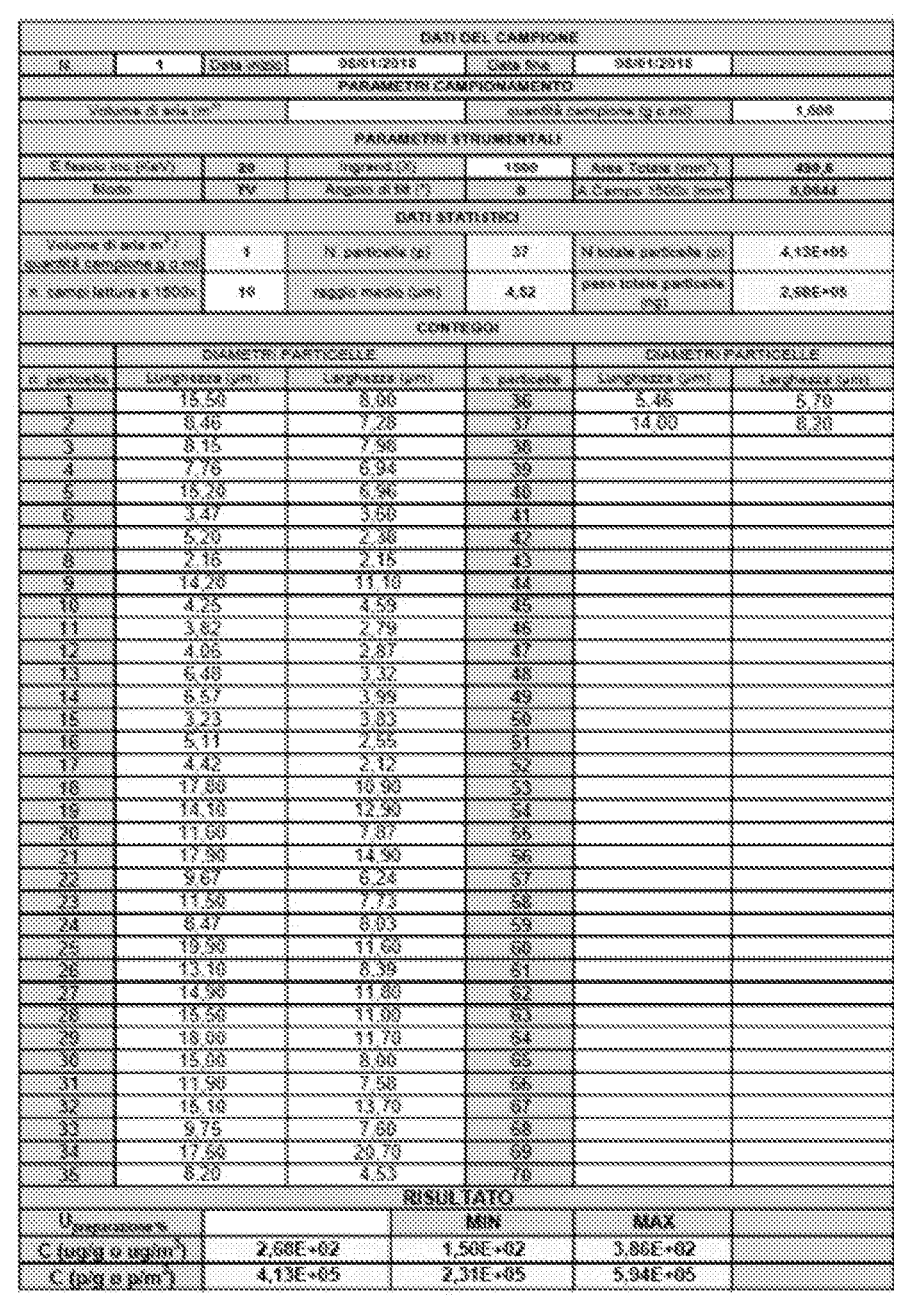
Figure 4:
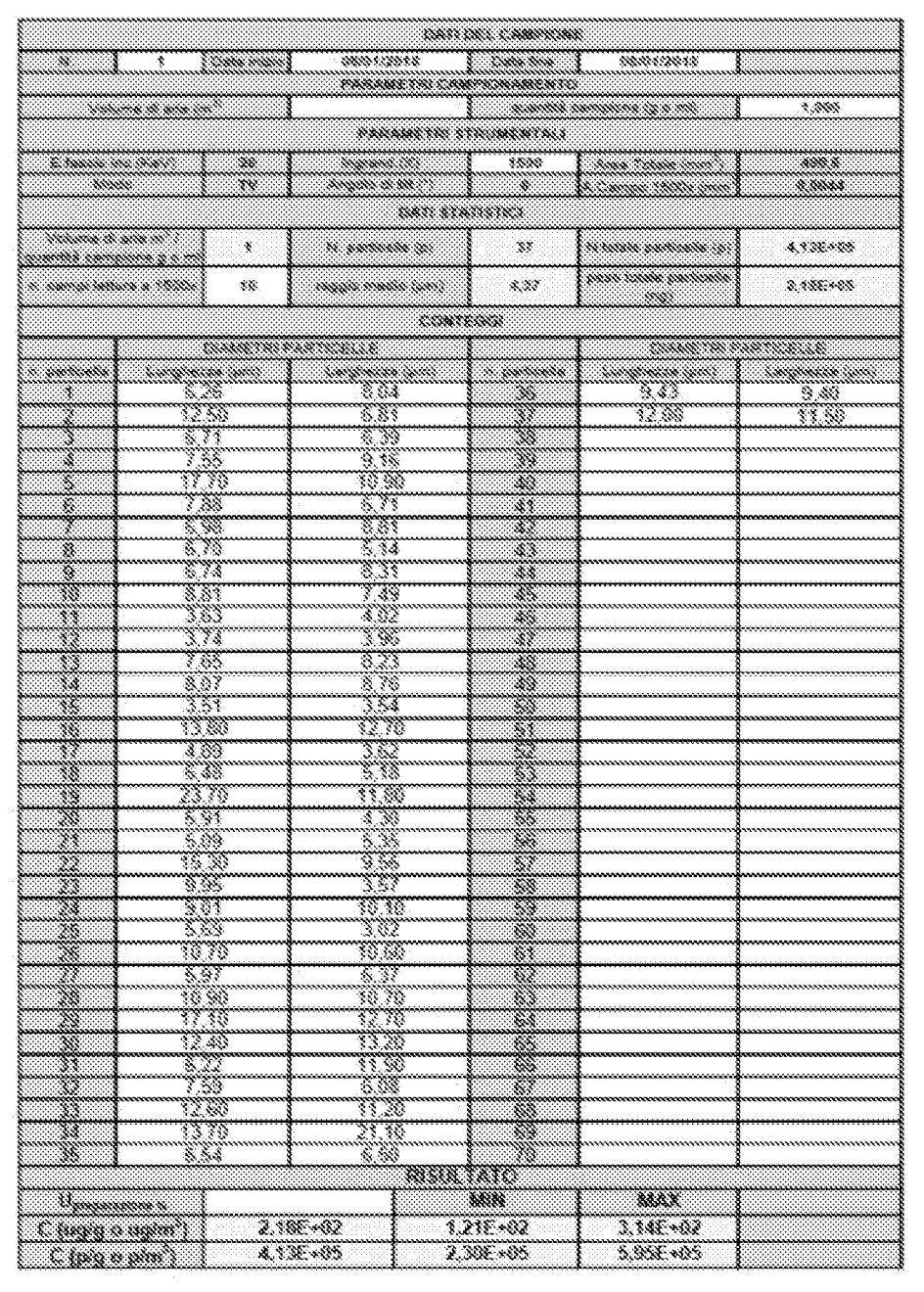
Figure 5:
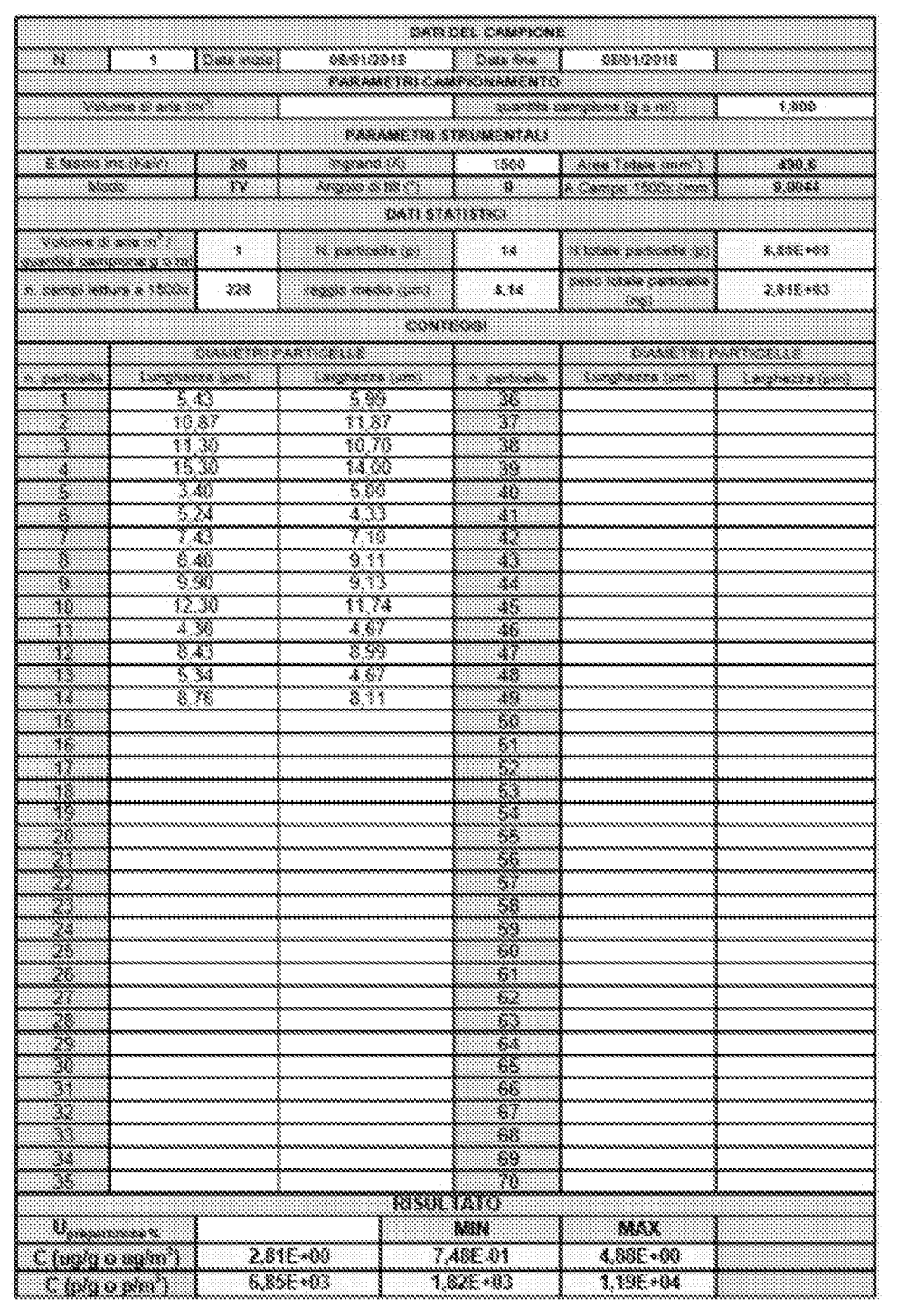

Conveniently, every measurement of length and width of each microplastic particle is reported in the calculation sheet in electronic format created especially for the application of the method for the extraction and the determination of microplastics in samples with organic and inorganic matrices, (MICROPLAST software, of which the exemplary screens can be found in FIG. 3-5). Said software automatically calculates the concentration of the microplastic particles, updating the results in real time according to the varying number and the dimensions of the microplastic particles counted and in function of the values of the other parameters, including quantity of samples analyzed, diameter of stub, etc. Moreover, the total weight of the microplastics contained in the sample is automatically estimated: the average radius of each particle; the volume, considering it as a regular sphere and, finally, the weight of the particle, considering the average density of the microplastics.

Conveniently, the determination of the microplastics in samples with organic and inorganic matrices is expressed in terms of number of particles on gram (or milliliter) of sample and cubic meter of air, both in terms of micrograms of microplastics in gram (or milliliter) of sample or cubic meter of air.

Conveniently, the extended uncertainty associated with the determination of the microplastics in samples with organic and inorganic matrices is expressed in confidence intervals (MIN and MAX). The evaluation of the experimental error in the measurement of concentration C of polyethylene in a massive sample is essentially due to two contributions: to the sampling statistic of N particles during the reading of the stub, assuming the casual Poisson distribution of the particles on the stub, and the width of the granulometric spectrum of the particles contained in the sample, so to the error made by adopting the average calculated only based on N particles identified as the average weight $p_m$ of the particles within the entire sample.

The experimental error on the concentration (or read error) can hence be evaluated using the relation $$\Delta C / C \approx \frac{\Delta N}{N} + \frac{\Delta pm}{pm}$$

where $$\frac{\Delta pm}{pm}$$

corresponds to the relative error associated with the average weight $p_m$ of the N particles identified and $$\frac{\Delta N}{N}$$

is the relative error associated with the N particles counted. Assuming a Poisson distribution for N particles counted, the relation $$\frac{\Delta N}{N}$$

can also be expressed as $$\frac{1}{\sqrt{N}},$$

while the relative error on the average weight $p_m$ of the N particles $p_i$ identified can be expressed using the standard error $$\sqrt{\frac{\Sigma_i (p_m - p_i)^{\wedge 2}}{N(N-1)}} \Big/ p_m.$$

Hence, the previous relation becomes $$\Delta C / C \approx \frac{1}{\sqrt{N}} + \sqrt{\frac{\Sigma_i (p_m - p_i)^{\wedge 2}}{N(N-1)}} \Big/ p_m$$

or $$U_{rel\ reading} \approx \sqrt{\left(\frac{1}{\sqrt{N}}\right)^2 + \left(\sqrt{\frac{\Sigma_i (p_m - p_i)^{\wedge 2}}{N(N-1)}} \Big/ p_m\right)^2}$$

Based on the following relations, it is deemed useful to consider, in order to obtain a more precise evaluation of the total uncertainties, the contribution of uncertainty deriving from the sample preparation procedure, which calls for the phases of grinding/blending, weighing, extraction, and dispersion on the stub. The resulting relation is the following:

$$U_{C_{rel}\%} = \sqrt{(U_p)^2 + (U_N)^2 + (U_{pr})^2}$$

or $$U_{C_{rel}\%} = \sqrt{(U_{lettrel})^2 + (U_{pr})^2}$$

where $U_p$ is the uncertainty associated with the average weight $p_m$ of the N particles identified $$\sqrt{\frac{\Sigma_i (p_m - p_i)^{\wedge 2}}{N(N-1)}} \Big/ p_m,$$

$U_N$ is the uncertainty associated with the N particles counted $$\frac{1}{\sqrt{N}}$$

and $U_pr$ is the contribution deriving from the uncertainty of preparation.

Conveniently, the software automatically calculates $U_p$ and $U_N$. The operator can estimate the uncertainty $U_{pr}$ by carrying out n repeatability tests and calculating the standard deviation. The $U_{pr}$, finally, must be inserted in the specific cell of the Software.

In a first embodiment, the method of this invention provides the extraction of microplastics from samples with a watery base and/or of an organic matrix belonging to the group comprising of human, plant, and animal biological tissues and liquids, pharmaceuticals, cosmetics, foods, mineral waters, waters destined for human consumption, ground waters, surface waters, sea waters, waters from pools and aquaculture installations, urban and industrial, and sewage, liquid wastes. Said samples with a watery base and/or organic matrix can be found under natural conditions or previously lyophilized.

The abovementioned samples with watery base and/or organic matrix are sampled according to known state-of-the-art methods.

Conveniently, the above mentioned samples with watery base and/or with organic matrix are pre-treated by means of grinding and/or blending, with the duration of the pre-treatment depending on the hardness of the sample, to obtain a homogenized sample, and then subjected to weighing.

An aliquot of the sample is transferred into a glass test tube—preferable with a volume of 16 ml, 100 mm tall, with a conical base, ground neck with a diameter of 16 mm and glass stopper—and an aliquot of strong acid in a 1:1 m/v or v/v ratio is added to carry out an acid digestion, or mineralization, for a duration of at least 24 h at a temperature of 60° C. In this first embodiment, the strong acid is nitric acid at 37%. The duration of the mineralization can be less than 24 h using a mineralizer in either a closed or open container. The success of the mineralization process makes it possible to obtain a somewhat transparent liquid.

The abovementioned stage of acid digestion makes it possible to destroy all the organic fraction of the sample through oxidation processes and increase the solubility of the mineral salts, otherwise present in crystal form, also amorphous, which may represent a factor of confusion during the stages of identification and quantification of microplastics.

Successively the mineralized sample is subjected to the liquid phase microplastics extraction stage as previously described in phases 1-8.

The stages of identification and quantification of the microplastics proceeds as previously described.

In a second embodiment, the method of this invention provides the extraction and the determination of airborne microplastics from air samples drawn from living and work environments, both indoors and outdoors.

The sampling and pre-treatment phase of the method proposed by this invention provides the use of filtering membranes in mixed cellulose esters with a diameter of 25 mm and a porosity of at least 0.8 μm. The filter holder used is exclusively in metal (aluminum or steel) and open-faced with a cylindrical hood, also in metal, that extends between 30 mm and 50 mm in front of the filter and allows the exposure of a circular area with a diameter of at least 20 mm.

The sampling stage for airborne microplastics can be conducted using two different methods: personal and environmental. The "personal" method provides the use of a sample with a good capacity to compensate load losses in order to obtain samplings even in intensely dusty conditions, making it possible to maintain, for the entire duration of the sampling, a capacity of at least 10% of the initial one. Conveniently, the filter holder is fixed in a zone near the airways with the opening facing downward. The aspiration flow is set between 1 and 5 l/min, preferably between 2 and 3 l/min.

The "environmental" method provides the positioning of the filter holder at a height of 150 cm from the ground, using a tripod with the hood facing downward; the sample connected is an environmental type with a constant high aspiration flow between 18 and 25 l/min. The sampling time depends on the aspiration flow and requires a minimum volume of air aspired of no less than 3000 liters. Conveniently, it is possible to insert the filters in special fraction collectors in order to sample only the particles with diameters less than 10 micrometers, or less than 2.5 micrometers.

Each sampled filter is positioned inside glass or metallic boxes; these are then positioned inside a sealed container so as to avoid generating impacts and to prevent the possibility of contamination of the filters with dust or other particles.

The abovementioned filter is subjected to pre-treatment prior to the acid digestion of the sample. Another advantage is that the abovementioned filter is fragmented by suitable devices in metal and then placed fragmented in a 16 ml transparent glass test tube with a height of 100 mm, conical base, ground neck with a diameter of 16 mm and glass stopper. Then the process provides the stages of acid digestion of the sample, extraction of microplastics in liquid phase, identification and quantification of the microplastics through scanning electronic microscope coupled with Energy Dispersive X-ray Analysis (SEM-EDX), as previously described above.

In a third embodiment, the method described in the present invention provides the extraction and determination of microplastics from soil samples.

The abovementioned microplastics from soil samples are subjected to a pre-treatment comprising the phases of:
  sifting with a sieve with a 10 mm metal mesh
  transfer of the sifted sample to a transparent glass test tube,
  acid digestion with strong acid, in a ratio of 1:1 m/v or v/v with the abovementioned sample, for a duration of at least 24 hours at a temperature of 60° C.,
  neutralization of the sample with sodium hydroxide 1 M,
  vacuum filtration by means of a filtering membrane in mixed cellulose esters with a porosity of 10 μm or 100 μm.

The method inherent to this invention requires that in the third embodiment, the successive phases of extraction of the microplastics follow the same methods described for the first embodiment of this invention, beginning with acid digestion.

The following examples can be considered, by way of example and not of limitation, of this invention.

Example 1

By way of example, below is a potential experimental application of the method for the extraction and the determination of microplastics in samples with organic and inorganic matrices for the determination of microparticles of polyethylene deriving from the wear of arthroplasty in periprosthetic tissues and in synovial fluid.

Among the various types of polyethylene, the one applied in orthopedics is ultra high molecular weight polyethylene (UHMWPE with a density of 0.96 g/cm$^3$), as it offers the best mechanical properties.

The purpose of the application of the method inherent to this invention is that of determining the presence of polyethylene particles in the synovial fluid and in periprosthetic tissues of patients with hip replacements, supposing a potential release of these particles following the mechanical wear of the acetabular insert.

Hence an intraoperative sample of periprosthetic tissue and a sample of synovial fluid were taken from a patient (CASE) subjected to an intervention to revise the hip replacement. In parallel, the same samples taken from a subject subjected to a primary arthroplasty hip replacement intervention were analyzed (CONTROL).

Simultaneously, a test was conducted to evaluate the recovery of a biological matrix similar in structure (animal muscle) with no contamination of polyethylene, previously fortified with microparticles of polyethylene obtained through the pulverization of an acetabular insert (standard or also known as material of reference).

An aliquot of 1 gram of each sample was transferred to a 16 ml transparent glass test tube with a height of 100 mm, conical base, ground neck with a diameter of 16 mm and glass stopper. A milliliter of nitric acid at 37% was then added to the samples and they were left to rest for 24 h, at a temperature of 60° C., to enable the chemical mineralization to take place as described in the method inherent to this invention.

Then 3 ml of ultra-pure water and 3 ml of dichloromethane (DCM) were added to the mineralized samples. The heterogeneous mixture was then effectively agitated using a high-speed vortex mixer for approximately 30 seconds. At this point the samples were centrifuged at 4000 rpm for 15 minutes with a benchtop centrifuge with mobile recipient and angle rotor. Successively, the more watery phase was transferred to a new test tube with characteristics identical to those described above. Following a further addition of another 3 ml of dichloromethane (DCM), the solution was again agitated by means of vortex and centrifuged for another 15 min at 4000 rpm with the same centrifuge. The watery phase was eliminated and the organic phase was combined with the previous one. The extract of each sample was left to evaporate to dryness, promoting the process only by means of heating with a plate set at a temperature of 70° C. Successively, the dry residue was mixed with 100 microliters of acetonitrile.

Then, after having "pipetted" multiple times using a glass Pasteur pipette in order to favor the dispersion of the particles, the suspension of each sample was transferred to a dedicated aluminum stub for scanning electronic microscope (SEM Specimen Stub) with a diameter of 25 mm, striving to distribute the solution on the entire surface of the stub. After having let the solvent evaporate, the stubs were metalized with gold and inserted into the sample positioning chamber of the SEM. More specifically, the Scanning Electronic Microscope (SEM) of Cambridge StereoScan 360 was used.

The abovementioned recovery tests, conducted by repeating the extraction and analysis of a white matrix fortified with 0.2 milligrams of micronized polyethylene twice, made it possible to identify particles with diameters that varied between 2 and 25 µm. The microanalysis highlighted that the chemical structure of the particles studied is on average composed of 92.5% in carbon. The remaining percentage consists exclusively of aluminum and copper, or by elements that make up the metallic support (stub) on which the extracted particles are dispersed (FIG. 2 and Table 1).

TABLE 1

Figure 2:
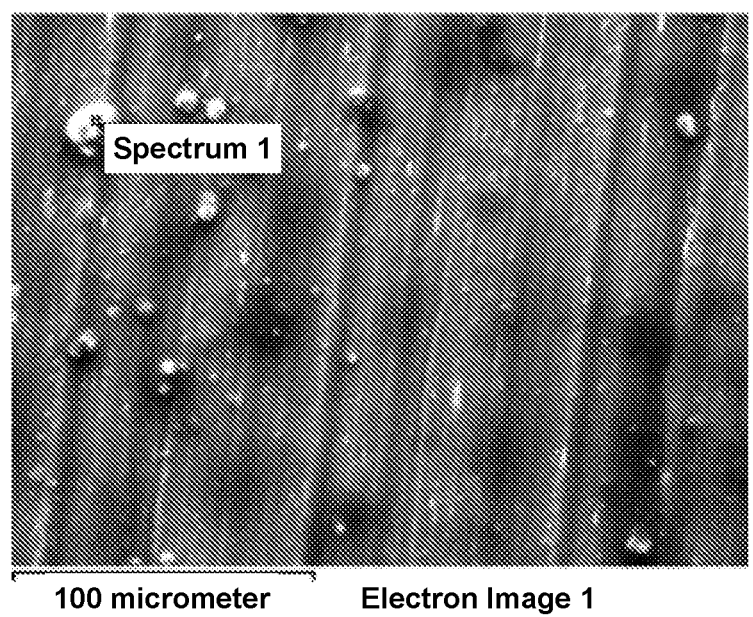
FIG. 2 is a SEM image of the standard sample of microplastics or reference material.

Chemical composition of the particle examined with microanalysis in FIG. 2

| Spectrum | In stats. | C | Al | Cu | Total |
|---|---|---|---|---|---|
| Spectrum 1 | Yes | 96.80 | 1.93 | 0.45 | 99.18 |
| Spectrum 2 | Yes | 95.08 | 4.52 | 0.00 | 99.60 |
| Spectrum 3 | Yes | 95.87 | 3.64 | 0.00 | 99.61 |
| Spectrum 4 | Yes | 91.34 | 8.02 | 0.25 | 99.30 |
| Spectrum 5 | Yes | 89.35 | 9.61 | 0.34 | 99.40 |
| Spectrum 6 | Yes | 93.82 | 5.32 | 0.26 | 99.33 |
| Spectrum 7 | Yes | 91.74 | 7.59 | 0.00 | 99.75 |
| Spectrum 8 | Yes | 81.87 | 17.37 | 0.51 | 99.53 |
| Spectrum 9 | Yes | 96.15 | 3.24 | 0.14 | 99.18 |
| Mean | | 92.45 | 6.80 | 0.22 | 99.47 |
| Std. deviation | | 4.70 | 4.68 | 0.20 | |
| Max. | | 96.80 | 17.37 | 0.51 | |
| Min. | | 81.87 | 1.93 | 0.00 | |

The quantitative analyses (FIG. 3 and FIG. 4), carried out via MICROPLAST software, have made it possible to calculate the average diameters of the particles, respectively equal to 4.52 µm and 4.37 µm. The concentrations of the two replicas were respectively equal to 268 µg/g and 218 µg/g. The average recovery calculated was equal to 121.5%.

The quantitative analysis of the non-fortified matrix (FIG. 5) made it possible to ascertain the low degree of contamination during the process. The concentration was equal to 2.81 µg/g.

Results of the Synovial Fluid (SINOVIA)

The application of the method inherent to this invention on samples of the "Case" and the "Control" highlights the significant differences between the synovial fluid relative to the "Case" and that relative to the "Control". The successive SEM analysis of the extract of the "Case" synovial fluid highlighted the presence of polyethylene particles with diameters varying between a few micrometers (approximately 1-10 µm) and three millimeters. The particles present all the morphological characteristics similar to those of the Standard, like irregular curvature of the edges and an apparently compact structure. The results of the microanalyses highlight a chemical composition made up almost exclusively of carbon with an average percentage of 95.1%. The remaining percentage consists exclusively of aluminum and copper, or by elements that make up the metallic support (stub) on which the extracted particles are dispersed. Rare traces of trace elements like K, Na, Ca, Cl were found (FIG. 6-7, Tables 2-3).

TABLE 2

Figure 6:
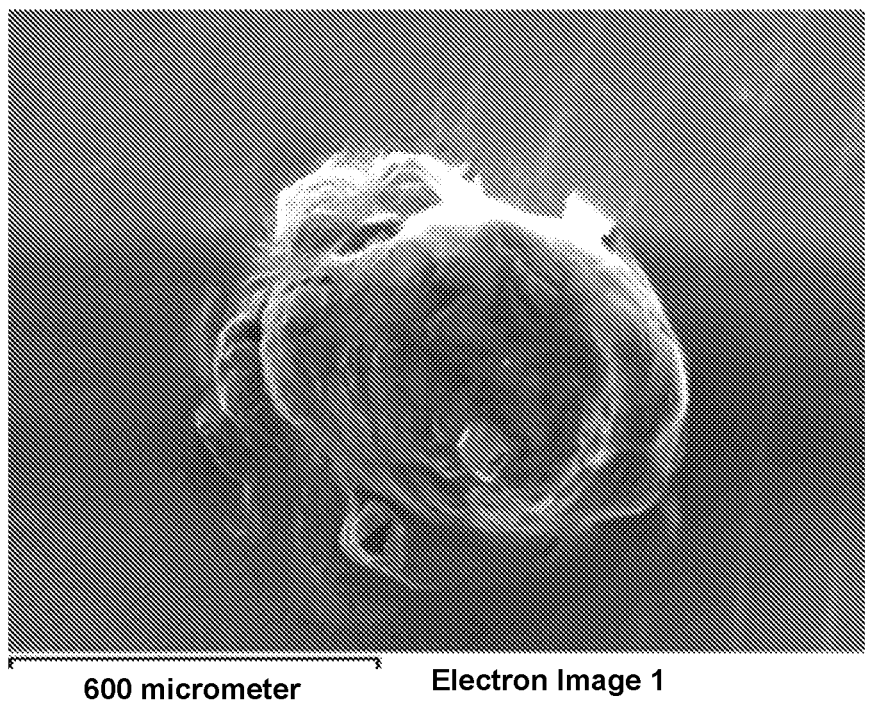
FIG. 6 is a SEM image of the synovial fluid (SINOVIA) of the "Case" extracted and dispersed on the stub, which visualizes a polyethylene particle with a dimension of 600× 450 μm, and average percentage of carbon equal to 98.4%.
Figure 7:
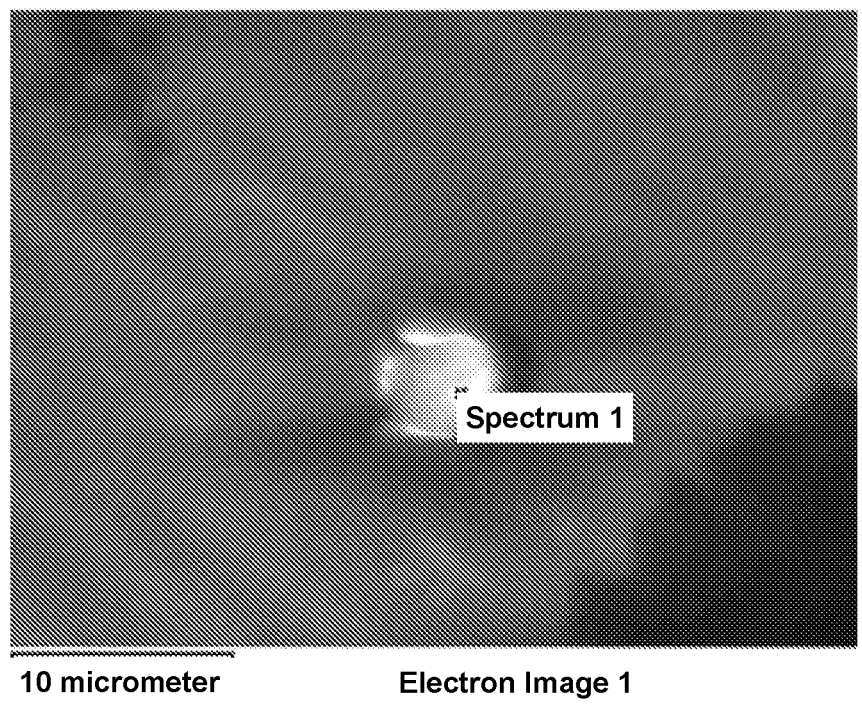
FIG. 7 is a SEM image of the synovial fluid (SINOVIA) of the "Case" extracted and dispersed on the stub, which visualizes a polyethylene particle with a dimension of 5×5 μm, and average percentage of carbon equal to 94.0%.

Percentage chemical composition of the particle in FIG. 6

| Spectrum | In stats. | C | Al | Cu | Total |
|---|---|---|---|---|---|
| Spectrum 1 | Yes | 97.06 | 1.31 | 0.38 | 99.68 |
| Spectrum 2 | Yes | 100.00 | 0.00 | 0.00 | 100.00 |
| Spectrum 3 | Yes | 98.36 | 0.26 | 0.20 | 99.88 |
| Spectrum 4 | Yes | 98.44 | 0.00 | 0.00 | 99.39 |
| Spectrum 5 | Yes | 97.99 | 0.66 | 0.26 | 99.87 |
| Mean | | 98.37 | 0.45 | 0.17 | 99.76 |
| Std. deviation | | 1.06 | 0.55 | 0.17 | |
| Max. | | 100.00 | 1.31 | 0.38 | |
| Min. | | 97.06 | 0.00 | 0.00 | |

TABLE 3

Percentage chemical composition of the particle in FIG. 7

| Spectrum | In stats. | C | Al | Cu | Total |
|---|---|---|---|---|---|
| Spectrum 1 | Yes | 93.73 | 5.26 | 0.71 | 99.70 |
| Spectrum 2 | Yes | 94.15 | 4.40 | 1.11 | 99.66 |
| Spectrum 3 | Yes | 94.21 | 5.10 | 0.47 | 99.78 |
| Mean | | 94.03 | 4.92 | 0.76 | 99.71 |
| Std. deviation | | 0.26 | 0.46 | 0.32 | |
| Max. | | 94.21 | 5.26 | 1.11 | |
| Min. | | 93.73 | 4.40 | 0.47 | |

The synovial liquid sample relative to the "Control" did not highlight the presence of polyethylene particles, demonstrating the effectiveness and efficiency of the method inherent to this invention.

Figure 8:
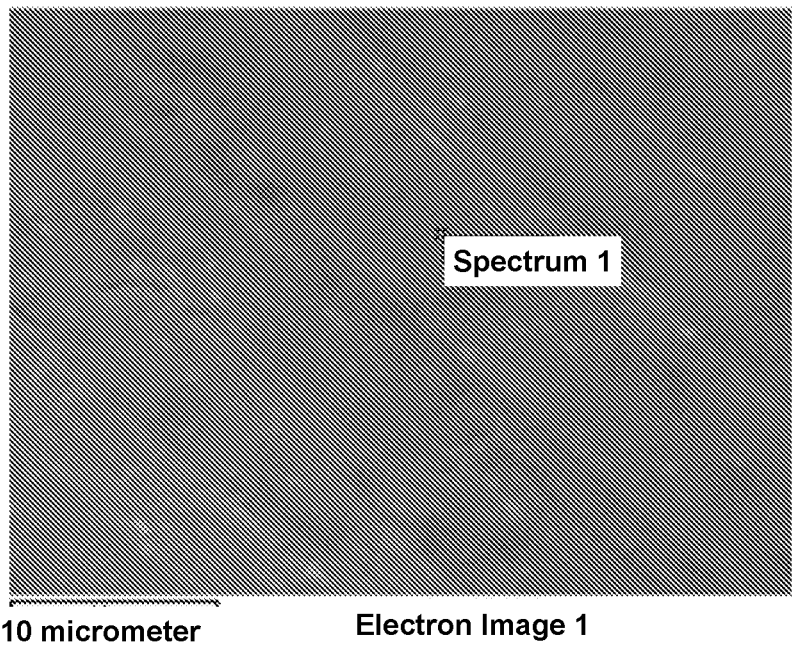
FIG. 8 is a SEM image of the sample of synovial fluid of the "control". The absence of polyethylene particles is evident.

It must be pointed out how no polyethylene particles were found in the sample of synovial fluid of the CONTROL. The microanalysis carried out in three different points of the STUB found that aluminum is the most abundant chemical element (FIG. 8 and Table 4). Therefore, the invention is effective and discriminating, identifying and quantifying polyethylene only in positive samples.

TABLE 4

Percentage chemical composition of the CONTROL in FIG. 8

| Spectrum | In stats. | C | Al | Cu | Total |
|---|---|---|---|---|---|
| Spectrum 1 | Yes | 18.97 | 79.05 | 1.98 | 100.00 |
| Spectrum 2 | Yes | 16.19 | 83.81 | 0.00 | 100.00 |
| Spectrum 3 | Yes | 0.00 | 100.00 | 0.00 | 100.00 |
| Mean | | 11.72 | 87.62 | 0.66 | 100.00 |
| Std. deviation | | 10.24 | 10.98 | 1.14 | |
| Max. | | 18.97 | 100.00 | 1.98 | |
| Min. | | 0.00 | 79.05 | 0.00 | |

Results on Tissue Sample

The application of the method inherent to this invention on samples of the "CASE" and the "CONTROL" highlights the significant differences between the tissue relative to the "CASE" and that relative to the "CONTROL".

The SEM analysis following the application of the invention on the tissues of the "CASE" highlighted the presence of polyethylene particles with much smaller dimensions than those found in the "CASE" synovial fluid (from 0.8 μm to 7 μm in diameter).

The particles analyzed presented all the morphological similarities of the Standard and of the microparticles found in the synovial fluid of the "CASE", like irregular curvature of the edges and an apparently compact structure. The results of the microanalyses highlight a chemical composition made up almost exclusively of carbon with an average percentage of 80.1%. The remaining percentage consists exclusively of aluminum and copper, or by elements that make up the metallic support (stub) on which the extracted particles are dispersed. Rare traces of trace elements like K, Na, Ca, Cl were found (FIG. 9 and Table 5).

TABLE 5

Figure 9:
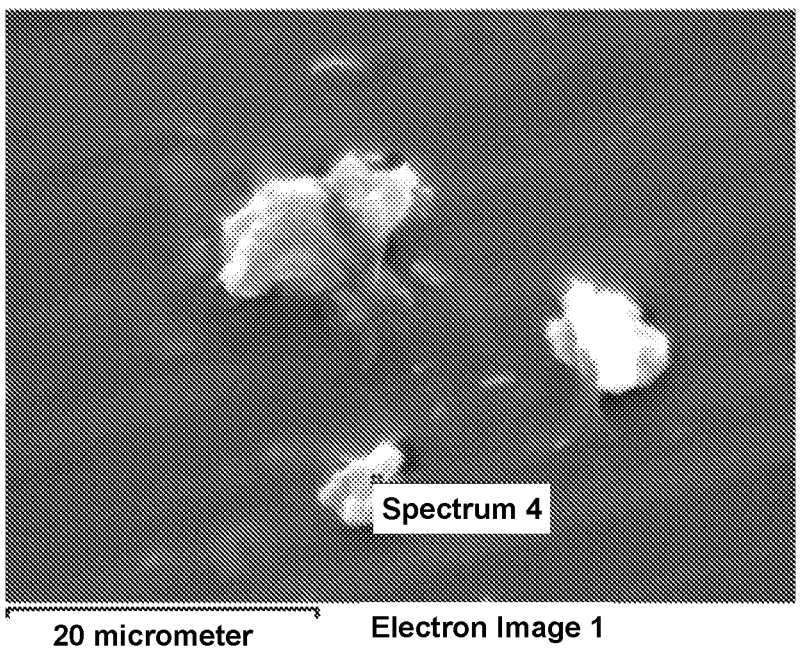
FIG. 9 is a SEM image of the tissue sample of the "Case" extracted and dispersed on the stub, which visualizes a set of particles with a maximum dimension of 5×15 μm.

Percentage chemical composition of the particles in FIG. 9

| Spectrum | In stats. | C | Al | Cu | Total |
|---|---|---|---|---|---|
| Spectrum 1 | Yes | 90.01 | 9.15 | 0.66 | 99.82 |
| Spectrum 2 | Yes | 93.21 | 7.15 | 0.25 | 99.61 |
| Spectrum 3 | Yes | 89.85 | 8.15 | 1.45 | 99.45 |

TABLE 5-continued

Percentage chemical composition of the particles in FIG. 9

| Spectrum | In stats. | C | Al | Cu | Total |
|---|---|---|---|---|---|
| Spectrum 4 | No | 90.89 | 8.49 | 0.71 | 99.99 |
| Mean | | 90.74 | 8.21 | 0.77 | 99.72 |
| Std. deviation | | 1.08 | 0.83 | 0.50 | |
| Max. | | 93.21 | 9.15 | 1.45 | |
| Min. | | 89.89 | 7.15 | 0.25 | |

Figure 10:
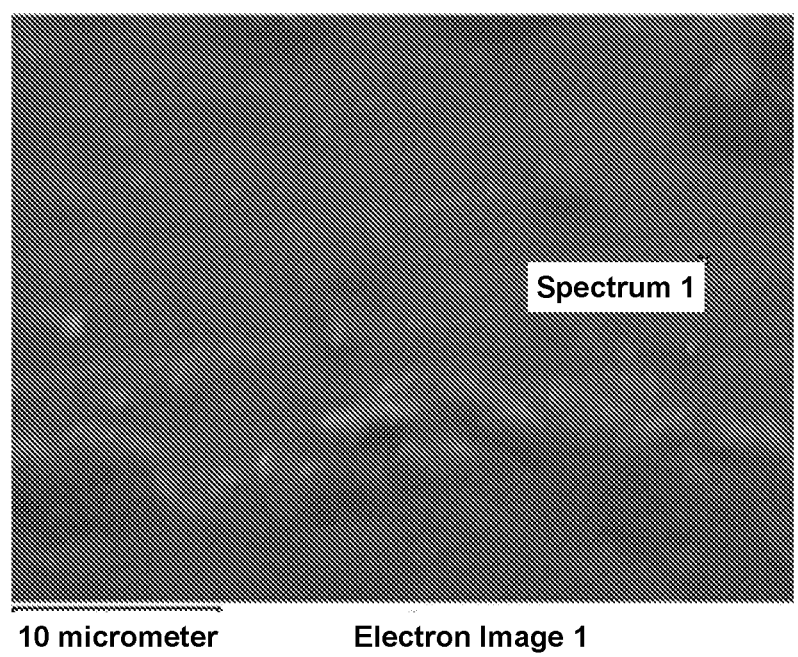
FIG. 10 is a SEM image of the tissue sample of the "Control" extract and dispersed on the stub. The absence of polyethylene particles is evident.

It is highlighted how no polyethylene particles were found in the tissue sample of the CONTROL. The microanalysis carried out in three different points of the STUB found that aluminum is the most abundant chemical element (FIG. 10 and Table 6). This result highlights the discriminatory effectiveness of the invention and denotes the absence of production of false positives and false negatives of the same, a fundamental characteristic in the pharmaceutical, forensic, food, medical/biomedical applications and quality control for all other types of samples for commercial or environmental use.

TABLE 6

Percentage chemical composition of the CONTROL in FIG. 10

| Spectrum | In stats. | C | Al | Cu | Total |
|---|---|---|---|---|---|
| Spectrum 1 | Yes | 28.87 | 70.26 | 0.87 | 100.00 |
| Spectrum 2 | Yes | 31.17 | 68.18 | 0.65 | 100.00 |
| Spectrum 3 | Yes | 27.08 | 71.63 | 1.29 | 100.00 |
| Mean | | 29.04 | 70.02 | 0.94 | 100.00 |
| Std. deviation | | 2.05 | 1.74 | 0.33 | |
| Max. | | 31.17 | 71.63 | 1.29 | |
| Min. | | 27.08 | 68.18 | 0.65 | |

The object of the invention is susceptible to numerous modifications and variants, all under the same concept of the inventive concept expressed in the attached claims.

All parts may be replaced with other technically equivalent elements, and the materials may differ according to needs, without departing from the scope of protection of the present invention.

Although the object was described with particular reference to the attached figures, the reference numbers used in the description and in the claims are used for a better understanding of the invention and do not constitute any limitation to the disclosed scope of protection.

BIBLIOGRAPHY CITED

Kandahari A M, Yang X, Laroche K A, Dighe A S, Pan D2, Cui Q; A review of UHMWPE wear-induced osteolysis: the role for early detection of the immune response; Bone Res. 2016 Jul. 12; 4:16014. doi: 10.1038/boneres.2016.14. eCollection 2016.

Choudhury D, Ranuša M, Fleming R A, Vrbka M, Křupka I, Teeter M G, Goss J, Zou M. Mechanical wear and oxidative degradation analysis of retrieved ultra-high molecular weight polyethylene acetabular cups. J Mech Behav Biomed Mater. 2018 March; 79:314-323. doi: 10.1016/j.jmbbm.2018.01.003).

Armstrong B L, Senyurt A F, Narayan V, Wang X, Alquier L, Vas G., Stir bar sorptive extraction combined with GC-MS/MS for determination of low level leachable components from implantable medical devices, J Pharm Biomed Anal. 2013 Feb. 23; 74:162-70. doi: 10.1016/j.jpba.2012.10.019. Epub 2012 Oct. 22.

Pokorný D, Slouf M, Horák Z, Jahoda D, Entlicher G, Eklová S, Sosna A., Method for assessment of distribution of UHMWPE wear particles in periprosthetic tissues in total hip arthroplasty, Acta Chir Orthop Traumatol Cech. 2006 August; 73(4):243-50.

Sosna A, Radonský T, Pokorný D, Veigl D, Horák Z, Jahoda D., Polyethylene disease Acta Chir Orthop Traumatol Cech. 2003; 70(1):6-16.

Narayan V S., Spectroscopic and chromatographic quantification of an antioxidant-stabilized ultrahigh-molecular-weight polyethylene, Clin Orthop Relat Res. 2015 March; 473(3):952-9. doi: 10.1007/s11999-014-4108-6.

Vesely F, Zolotarevova E, Spundova M, Kaftan F, Slouf M, Entlicher G., Simple colorimetric methods for determination of sub-milligram amounts of ultra-high molecular weight polyethylene wear particles, Acta Biomater. 2012 May; 8(5):1935-8. doi: 10.1016/j.actbio.2012.01.010. Epub 2012 Jan. 18.

Wright S L, Kelly F J. Plastic and Human Health: A Micro Issue? Environ SciTechnol. 2017 Jun. 20; 51(12):6634-6647. doi: 10.1021/acs.est.7b00423

The invention claimed is:

1. Method for the extraction and the determination of microplastics in samples with organic and inorganic matrices, including the fundamental stages of:
   a) sampling and pre-treatment,
   b) acid digestion of the sample,
   c) extraction of microplastics during the liquid phase,
   d) identification and quantification of the microplastics,
in which said acid digestion is conducted with strong acid, in a ratio of 1:1 m/v or v/v with the abovementioned sample, for a duration of at least 24 hours at a temperature of 60° C., and in which said extraction stage of the microplastics in liquid phase includes the following phases:
   1. mix an aliquot of ultra-pure water with said sample treated with strong acid, in a ratio of 1:3 m/v or v/v, to obtain a liquid mixture;
   2. mix a first aliquot of non-polar halogenated solvent with said liquid mixture in a ratio of 1:3 m/v or v/v, to obtain a heterogeneous liquid mixture;
   3. agitate said heterogeneous liquid mixture for 30 s and centrifuge it at 4000 rpm for 15 minutes to obtain two fractions: A and B, in which fraction A is watery and fraction B is organic;
   4. separate the watery fraction A from the organic fraction B;
   5. add a second aliquot of non-polar halogenated solvent to the watery fraction A to obtain a second heterogeneous mixture;
   6. agitate said second heterogeneous liquid mixture for 30 s and centrifuge it at 4000 rpm for 15 minutes to obtain two liquid phases: C and D, in which fraction C is watery and fraction D is organic;
   7. recombine the organic fractions B and D and then evaporate to dryness at a temperature of 70° C., to obtain an extract of microplastics;
   8. suspend said extract of microplastics in acetonitrile with a volume between 100 and 500 microliters,
and in which the stage of the identification and quantification of the microplastics involves the transfer of said extract suspended in acetonitrile on metallic support and its successive metallization with gold,
and characterized by the fact of measuring the dimension and counting a plurality of microplastics, as the reading area measures 1 mm$^2$, by means of electronic microscope coupled with energy dispersive X-ray analysis.

2. Method according to claim 1 in which said microplastics have dimensions less than 500 µm, more specifically with dimension less than 100 µm, and even more specifically with dimensions between 1 and 5 µm.

3. Method according to claim 1 in which said strong acid is selected from the group comprising hydrochloric acid, nitric acid and sulfuric acid.

4. Method according to claim 1 in which said non-polar halogenated solvent is selected from the group comprising dichloromethane and chloroform.

5. Method according to claim 1 in which said sampling stage is conducted on samples with a watery base or of an organic matrix comprised in the group consisting of human, plant, and animal biological tissues and liquids, pharmaceuticals, cosmetics, foods, mineral waters, waters destined for human consumption, ground waters, surface waters, sea waters, waters from pools and aquaculture installations, urban and industrial, and sewage, liquid wastes, and is characterized by an optional successive pre-treatment of the abovementioned samples by means of grinding and/or blending.

6. Method according to claim 1 in which said sampling stage is conducted on air samples containing microplastics.

7. Method according to claim 6 characterized by the fact that said sampling stage is conducted by means of filtering membranes in mixed cellulose esters with a diameter of 25 mm and porosity no higher than 0.8 µm, and characterized by the fact that it entails the use of an open-faced metallic filter holder with a cylindrical metal hood with an extension measuring between 30 and 50 mm in front of the filter.

8. Method according to claim 7 characterized by the fact that said filtering membranes are subjected to a pre-treatment comprising the additional phases of:
   fragmenting of said filtering membrane with metal cutting tool,
   transfer of the fragments of filtering membrane into a transparent glass test tube.

9. Method according to claim 1 in which said sampling stage is conducted on soil samples containing microplastics.

10. Method according to claim 9 characterized by the fact that said soil samples are subjected to a pre-treatment comprising the additional phases of:
   sifting with a sieve with a 10 mm metal mesh,
   transfer of the sifted sample to a transparent glass test tube,
   neutralization of the sample with sodium hydroxide 1M following a first stage of acid digestion with strong acid, in a ratio of 1:1 m/v or v/v with the abovementioned sample, for a duration of at least 24 hours at a temperature of 60° C.,
   vacuum filtration by means of a filtering membrane in mixed cellulose esters with a porosity of 10 µm or 100 µm.

* * * * *